US006447461B1

(12) United States Patent
Eldon (10) Patent No.: US 6,447,461 B1
(45) Date of Patent: Sep. 10, 2002

(54) METHOD AND SYSTEM FOR CONDUCTING A HEARING TEST USING A COMPUTER AND HEADPHONES

(75) Inventor: Steven Anthony Eldon, San Rafael, CA (US)

(73) Assignee: Sound ID, Palo Alto, CA (US)

( * ) Notice: Subject to any disclaimer, the term of this patent is extended or adjusted under 35 U.S.C. 154(b) by 9 days.

(21) Appl. No.: 09/707,662

(22) Filed: Nov. 7, 2000

Related U.S. Application Data (60) Provisional application No. 60/165,447, filed on Nov. 15, 1999.

(51) Int. Cl.[7] ................................................ A61B 5/00
(52) U.S. Cl. ........................................ 600/559; 73/585
(58) Field of Search .............................. 600/300, 559; 73/585

(56) References Cited

U.S. PATENT DOCUMENTS

| | | | | |
|---|---|---|---|---|
| 4,847,763 A | * | 7/1989 | Moser et al. ................ | 600/559 |
| 5,825,894 A | * | 10/1998 | Shennib ....................... | 381/60 |
| 5,928,160 A | | 7/1999 | Clark et al. .................. | 600/559 |
| 6,139,507 A | * | 10/2000 | Jeng ............................ | 600/559 |

OTHER PUBLICATIONS

Minifie et al., *Normal Aspects of Speech, Hearing, and Language* ("Psychoacoustics", Arnold M. Small, pp. 343–420), 1973, Prentice–Hall, Inc.

* cited by examiner

*Primary Examiner*—Kevin Shaver
*Assistant Examiner*—Charles Marmor, II
(74) *Attorney, Agent, or Firm*—Mark A. Haynes; Haynes Beffel & Wolfeld LLP (57) ABSTRACT

A hearing analyzer, and a user-operated, user-calibrated audiological test system which comprises software, a calibrator, and specified headphones. The frequency response of the headphones is measured. The soundcard of a computer is used to generate audiological test signals, and either the actual output level of those signals or the analysis of results is compensated by software to the frequency response of the headphones. The calibrator allows an accurate calibration level to be established for the soundcard output. The software provides for using the method of adjustment test procedure to perform several audiological tests.

20 Claims, 7 Drawing Sheets

METHOD AND SYSTEM FOR CONDUCTING A HEARING TEST USING A COMPUTER AND HEADPHONES

RELATED APPLICATION DATA

Applicant claims the benefit of U.S. Provisional Application No. 60/165,447; filed Nov. 15, 1999; entitled EAR Q REFERENCE HEARING SYSTEM, and incorporates such Provisional Application by reference, as if it were fully set forth herein.

BACKGROUND OF THE INVENTION

1. Field of the Invention

The present invention relates to hearing test equipment designed for musicians, recording studio engineers, audio professionals, and everyone else who desires to obtain for themselves accurate information about their hearing at their own recording facility or at home, using computer equipment and headphones.

2. Description of Related Art

Professional and home recording equipment that is based on digital technologies has significant flexibility. As of 1999, most commercial recording studios have integrated computer-based music recording and/or editing capabilities. These facilities are often staffed by engineers who have worked with sound at high volume for many decades, and so have some degree of hearing impairment (due to aging and to noise exposure) that they are not aware of because they do not, as a rule, get their hearing tested. Therefore, it is desirable to integrate hearing test procedures and equipment smoothly into these professional environments to allow these seasoned professional engineers to obtain accurate, confidential information about their hearing by using the computer in their facility. In contrast to conventional Audiometry, which is concerned with the frequency range of speech (125–8,000 hz), the use of computer equipment allows for self tests over the full range of audible frequencies present in music (20–20,000 hz). Since audio engineers use their own hearing in their profession as the reference standard, a hearing test can act as a "reference check" similar to a guitar tuning measurement device or a sound level measurement device.

In addition to large commercial recording facilities, every year hundreds of thousands of new, personal, home-based recording facilities are built that use Personal Computers as the primary recording and editing device. The numbers of such "project studios" is increasing so rapidly primarily because the cost of purchasing Professional Audio recording equipment has decreased dramatically. Digital technology has now placed Professional Audio recording equipment in the hands of the general musician population. Yet very few of these semi-pro equipment buyers have a good understanding of their own hearing. They therefore may work at a disadvantage, sometimes making adjustments to their equipment without realizing why. There is a need for these users of digital recording equipment to gain the same level of understanding about their hearing as the professionals.

Those familiar with the art know that stand-alone compact disks (CDs) with test tones are not accurate for all headphones, due to the wide range of variation in frequency response of headphones. Similary, it has been impractical in the prior art to establish a calibration reference at for example 1 khz, for each and every set of headphones, and then ensure that the signal levels at all other frequencies are also known. This is due for example to differences in coupler behavior and response, coupling pressure, and resonance peaks and dips that may exist. Without accurate tone generation either calibration or audiological test results that follow cannot be accurate.

Finally, the standard "Forced Response" method of audiological testing, where the actual level of each test frequency is varied by automation or by the Audiologist, is quite time consuming. It is desirable therefor to allow testing wherein the user directly controls the output level of each test frequency, which is a great deal faster and therefore easier to incorporate into engineers' busy schedules—and hence more likely to be used. Well established research from Bekesy onward has shown the Method of Adjustment to be faster, with greater test-retest reliability, than the Forced Response method. See the chapter, "Pyschoacoustics," by Arnold M. Small, in the book "Normal Aspects of Speech, Hearing, and Language," Edited by Minifie, Hixon, and Williams, 1973: New Jersey, Prentice-Hall, Inc that describes the Bekesy method in some detail as it compares to other audiometric test procedures.

SUMMARY OF THE INVENTION

The present invention provides a hearing analyzer method and apparatus, and a user-operated, user-calibrated audiological test system which comprises software, a calibrator, and specified headphones. The frequency response of the headphones is measured. The soundcard of a computer is used to generate audiological test signals, and either the actual output level of those signals or the analysis of results is compensated by software to the frequency response of the headphones. The calibrator allows an accurate calibration level to be established for the soundcard output. The software provides for using the method of adjustment test procedure to perform several audiological tests.

In one embodiment, the invention provides a method for performing a hearing test using a system including a computer producing audio signals, headphones and volume control for the audio signals. The headphones are characterized by a data set including drive voltages for corresponding test frequencies at which a constant sound pressure level (SPL) is generated by the headphones. Further, the headphones are characterized by a calibrated drive voltage at a particular reference frequency which produces a particular sound pressure level output by the headphones. The method comprises coupling audio signals from the computer to the input of a calibration device which translates an input audio signal to output drive voltages. In addition, the output of the calibration device is coupled to the headphones. The output of the system is set to particular frequency, such as 1 kHz. The volume control for the audio signals at the particular frequency is adjusted until the calibration device produces the calibrated drive voltage on its output. With the volume control set for the system at the adjusted level, the user is prompted through a hearing test in the test frequencies, while the output of the system is controlled according to a data set characterizing headphones. In various embodiments, the user is prompted using a graphical user interface. For one example, the graphical user interface includes a graphical input construct appearing like a set of sliders for a set of frequencies. Software is used to control the computer to output tones according to frequencies in the set of frequencies in response to adjustment by the user of an indicator on the graphical input construct for each of the tones. The graphical user interface further includes resources for displaying results of the test, such as in the form of a graphical audiogram.

In one embodiment, the hearing test comprises a minimum audibility test. In yet another embodiment, the hearing test comprises an equal loudness test.

The calibrator according to one embodiment includes indicator light on the device which indicates when the calibrator is producing the calibrated drive voltage. The step of adjusting includes adjusting the volume control until the indicator light is illuminated. In one embodiment, first, second and third indicator lights are provided on the calibrator. The first indicator light indicates that the output of a calibration device is below the calibrated drive voltage. The second indicator light indicates that the output of the calibration device is about equal to the calibrated drive voltage. The third indicator light on the calibration device indicates that the output of the calibration device is above the calibrated drive voltage.

In yet another embodiment of invention, an apparatus is provided for conducting hearing tests. The apparatus includes a calibration device as described above, and computer software stored or provided to the computer in a machine readable medium, such as memory the computer, or a medium which is readable by the computer.

In one embodiment, the invention is a user-operated, user-calibrated, computer-based system that generates and administers full range (20–20,000 hz) audiometric testing after accurately establishing a reference calibration level.

Other aspects and advantages of the invention can be seen upon review the figures, the detailed description and the claims which follow.

DETAILED DESCRIPTION

The overall function of one preferred embodiment of the invention is to present audiometric signals to the ears by using a personal computer, calibrator, software, and headphones, preferably recording studio quality headphones, to obtain information about the sensitivity, dynamic range, and loudness perception characteristics of human hearing over the full range of audible frequencies (20–20,000 hz). The provided calibrator is used to accurately establish a reference calibration level from which other levels will be interpolated by the user, via the software. The computer's soundcard is used to generate different types of audio signals, and the provided software both compensates for the frequency response of the specified headphones and controls the frequency and volume level of the audio signals using a special User Interface. The actual selection of both frequency and volume level is performed directly by the user via several "Method of Adjustment" test procedures. This combination of features constitutes a hearing test system that can be used in any recording studio or similar computer-based audio-equipment environment to provide accurate audiological tests.

Those familiar with the art will realize that there are a number of significant obstacles to using a personal computer to conduct self tests on hearing. 1) The presence of noise can mask the audiological test tones, and so these masking effects must be accounted for or removed. 2) Harmonic distortion occurs when a sine wave signal is digitally attenuated close to the capacity of the computer soundcard's dynamic range, and so some strategy must be developed to correct for this. 3) Commercially available soundcards vary in frequency response and distortion characteristics, and the variations must be measured and compensated for, if necessary. 4) All commercially available headphones differ enormously from each other in terms of frequency response, and so are not at all interchangeable at will, but must be carefully measured, and compensated for, or reduced to a single constant make and model that possesses known and consistent frequency response characteristics, just as in current Audiometric practice. 5) Calibration that is established by some means that has no reference to existing audiological standards or results is meaningless, and therefore exactly how a PC-based system is calibrated must conform to current audiometer calibration practices.

Headphones suitable for use according to the present invention are selected by 2 steps:

1) Determine typical recording studio ambient noise levels that include computer and machine fan noise, and 2) determine the degree to which the selected headphones attenuate that noise. The objective is to provide enough predictable attenuation via the specified headphones so that there exists a high degree of certainty about the accuracy of hearing test results to be obtained with the invention in the intended recording studio environments. After selecting suitable headphones, it is necessary to determine the suitability of selected computer soundcards for providing audiological test signals by analyzing those cards for frequency response, distortion, and stability at various signal levels, and determining how the signal level can be attenuated with a minimum of resultant distortion. With a suitable system including a computer with a sound card or equivalent hardware for producing audio signals, headphones and a volume control for the headphones, the system is used for hearing tests by determining the frequency response characteristics of the specified headphones, determining the drive voltage that will generate a target calibration value in dB SPL (ie, 94 dB) using a 1 kHz calibration sine tone in the headphones, and utilizing a calibration device to indicate by bulb light, meter reading or other indication, that this proper voltage is being sent to the headphones at 1 kHz, so that the specified headphones generate the target calibration level (ie, 94 dB SPL), as measured by established audiometric coupler; and implementing software that causes the computer's soundcard to generate audio signals appropriate for audiological testing; allows the user to manually control the actual output of those signals during testing; and, during these functions, automatically compensates for the frequency response of the headphones either as adjustment of signal level or adjustment of results.

Figure 1:
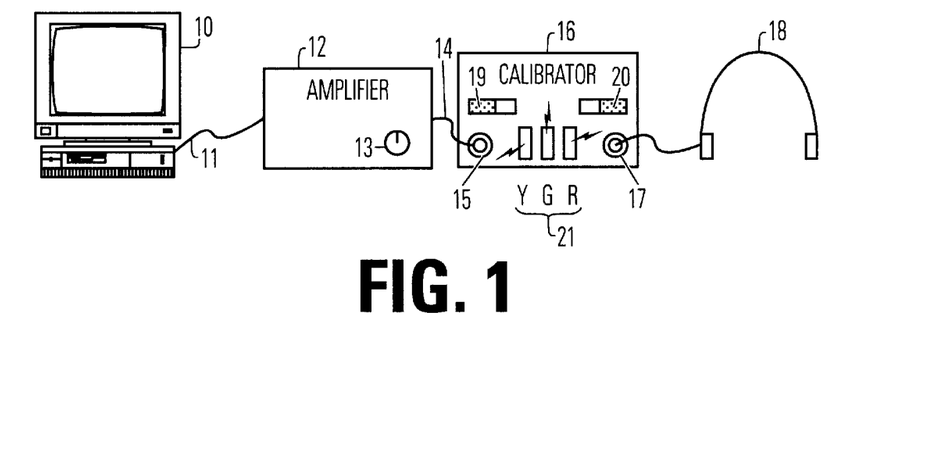
FIG. 1 is a simplified diagram of a system for conducting a hearing test according to the present invention.

FIG. 1 illustrates a basic system according to the present invention. The system includes a computer 10, including a soundcard, or equivalent processing resources, to generate output audio signals on line 11. The output of a computer soundcard is connected to an amplifier 12, such as found on an external mixer, a stand alone amplifier, or the headphone jack of the computer's speakers, which typically has its own volume control 13. This amplifier's headphone output on line 14 is connected to the input 15 of the calibrator 16, and headphones 18 are connected to the output 17 of the calibrator 16. Alternatively, the output of the computer's soundcard is connected directly to the input 15 of the calibrator 16, if the soundcard is sufficiently powerful to drive the headphones and the output level is controllable. In this case, the computer's own manual volume control would be used to establish calibration level.

The calibrator includes an on/off switch 19, a set of indicator lights 21 which comprise yellow, green and red light emitting diodes, and selector switch 20 used for setting the calibrator to a desired headphone type to be calibrated. A more detailed diagram of one embodiment is provided below with respective FIGS. 7A and 7B. The calibrator may be implemented using digital or analog components, or a combination of digital and analog components. Further, the calibrator may be designed to handle one, or more than 1, headphone type as suits the needs of a particular implementation.

Figure 2:
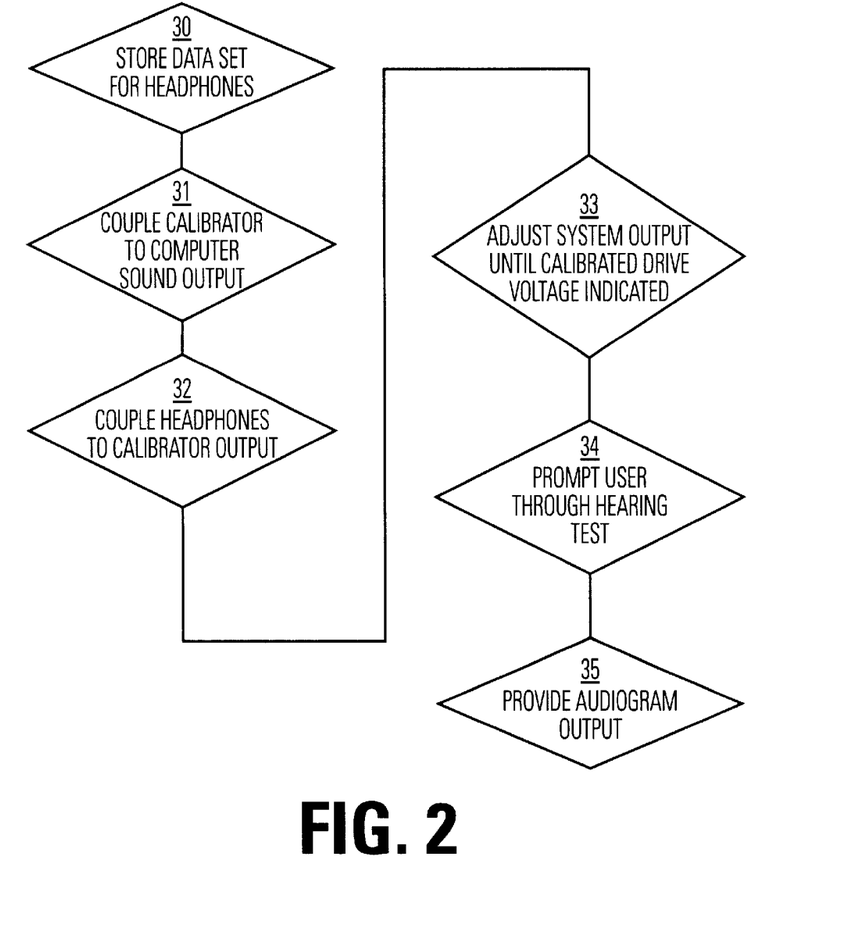
FIG. 2 is a basic flow diagram for conducting the test according to the present invention using a system of FIG. 1.

A basic flow chart for the process of conducting a hearing test according to the present invention is shown in FIG. 2. The order of the steps can be changed as suits a particular embodiment. The process begins by storing a data set characterizing the frequency response of the headphones for sound pressure levels at various input drive voltages over the range of frequencies to be utilized in the test (step 30). A calibrator is coupled to the computer sound output (step 31). The headphones are coupled to the calibrator output (step 32). The system output is adjusted until the calibrated output drive voltage is indicated by the calibrator (step 33). A user is prompted through a hearing test using a graphical user interface in a preferred embodiment, controlled by software in the computer 10 (step 34). An audiogram output is provided to user at the end of the test (step 35). More details of various embodiments of the invention are provided below.

In support of implementation of the invention, studio ambient noise analysis, and soundcard analysis were preformed. A description of this analysis is provided for background information.

Studio ambient noise analysis: Measurements were taken of several "noisy" project studios located in private homes and several professional recording studios to determine average background noise. Measurements were made using a Bruel and Kjaer Artificial Ear containing a Larson Davis 2559½" pressure microphone with preamp, through a Bruel and Kjaer 2607 Measuring Amplifier, into a Event Electronics 20-bit Gina soundcard inside of a 400 mz Pentium II computer. Analysis was performed in that computer by SoundTechnology's SpectraRTA software.

The studio with the highest noise level was selected, as containing the highest noise level that would reasonably have to be dealt with, and the degree to which the selected headphones attenuated that noise was measured. This was accomplished by placing the selected headphones on the 4153 coupler and making a new measurement of the studio noise as blocked by those headphones. The reasoning behind this choice is that most recording studio environments are fairly quiet, so if the noisiest one was chosen there would be reasonable assurance that the results would be transferable to a large number of locations.

In this manner it was determined that, even in the noisiest studio, most ambient noise was caused by computer fans (in this instance 3 seperate fans, which is arguably an unrealistically high number) and was concentrated in the 125–250 hz spectral regions. It was also determined that, using the specified headphones, sufficient attenuation of this noise was achieved in all frequencies above 500 hz. It was found that in all 1-octave frequency bands, the tested noise level after attenuation falls below the ANSI standards for allowable noise in hearing test booths. Since the frequencies of 125 and 250 are allowed to be omitted for Standard Audiometric Tests, this proved that the selected headphones would provide for accurate audiometric testing in most recording studio environments.

Soundcard Analysis: A number of PC soundcards are measured for inherent noise floor, harmonic distortion, frequency response, and linearity. Tests are performed by first connecting the soundcard's Input to its Output via a stereo ⅛" patch cable, and then utilizing the SoundTechnology Test Software. Pink noise and sine tones are sent out of the soundcard's output, and measured at its input. This methodology allows for precise measurements. Soundcards that exhibit excellent characteristics are selected as being appropriate for audiological test use, and noted in the Ear Q Software. For example, selected cards all display <1 dB inherent noise in the test computer (above); <0.01% harmonic distortion; a flat frequency response from 30 to 16 khz with predictable fall offs beyond that range; and perfect linearity from 90 dB to 10 dB.

The manner in which signal level is controllable by the soundcard is also determined, for later use in the software application. Specifically, the digital values are determined that control the analog output of the signal level by the Microsoft Windows Mixer Utility. For example, if the digital value of 5116 causes the MS Mixer to attenuate the analog output of the signal by 30 dB while the digital signal is still left at full scale, then this value is noted for later use in the Ear Q Software. This method of attenuating the output level of the audio signal provides for a widened dynamic range with lower harmonic distortion out of most soundcards.

It should be noted that as digital technology advances and the bit resolution and hence dynamic range of computer soundcards increase, it will be possible to utilize soundcards that may not exhibit perfectly flat frequency response characteristics by having the software compensate for the inaccuracies.

Figure 3:
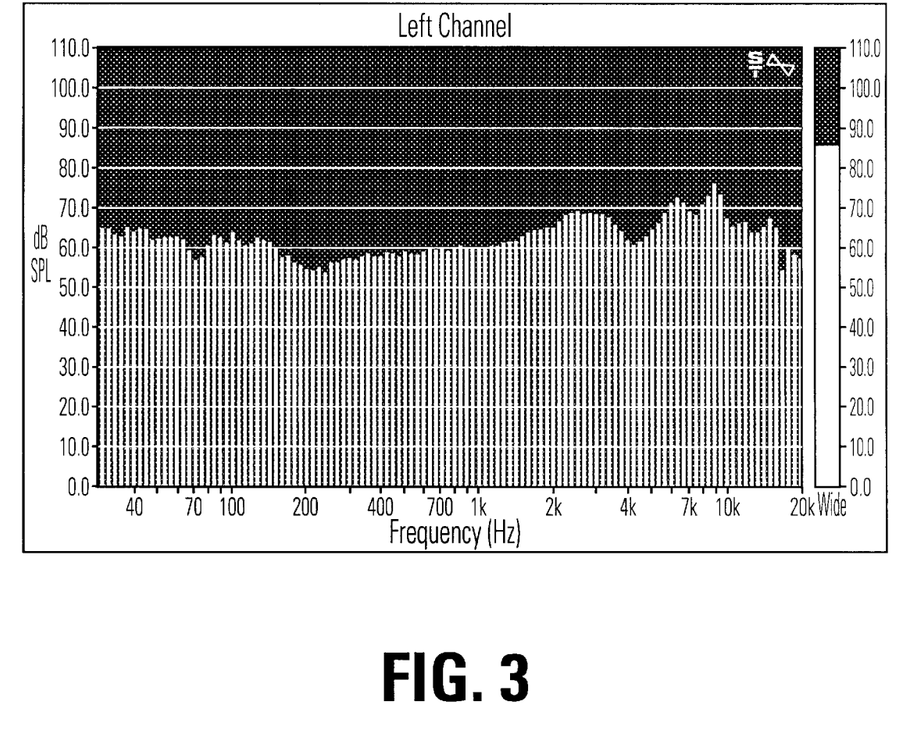
FIG. 3 illustrates a data set characterizing a set of headphones for use with the hearing test device of the present invention.

Conventional audiometric headphones have a limited frequency response. In order to test extended range frequency perception (ie, that of music), it is essential to use headphones with a suitably wide response. The frequency response characteristics of several dozen different professional studio monitor headphones of sealed design are tested, using conventional Audiometer Calibration Test Equipment. The left driver of each set of tested headphones is placed on a Bruel & Kjaer 4153 Coupler; which houses a Larson Davis 2559 Pressure Mic and B&K 2661 Preamp; that is connected to a B&K 2607 Measuring Amplifier and then to an Even Gina 20-bit soundcard inside of a 400 mhz Pentium II PC. The PC's Soundtechnology RTA software program uses the input and output of the Gina soundcard. Pink noise and sine tones are sent from the signal generator application of the RTA program via the output of the soundcard, through an external amplifier, into the headphones and SPL measurements are taken. Similarly accurate measuring equipment may be used. Headphones that have been tested in this manner include Beyerdynamic 831, 250, and DT 770; Sony MDR 7506, and 7502; Audio Technica ATH-M40fs; Sennheiser HD25 and HD 250 Linear; Koss QZ99, r-80, A-130, and A-250; AKG 290; and others. For initial design purposes, the Beyerdynamic DT 770 Pro has been selected. Different headphones may be used, or added. FIG. 3 illustrates the data set of one set of typical headphones, such as the Beyerdynamic DT 770 Pro.

Note the characteristic response of this headphone shown in FIG. 3, as referenced to the eardrum as represented by HATS response. The deviations from 1 khz are noted, and entered into the software program to be used to either modify the signal level or to modify the calculation and display of the hearing test results. For example at 3000 Hz, the Beyer headphones generate 8 dB more signal at this frequency than they generate at 1 kHz, referenced to the eardrum. A value of 8 dB is entered into the software program, and can be used in several ways. First, it may be used to adjust the actual output level of the signal. Since the Ear Q Faders adjust SPL and not hearing level (HL), when the 3000 Hz frequency is selected, 8 dB could be subtracted from the value that the fader is set at. With the fader set at 40 dB, the signal coming out of the headphones would be 48 dB; the software would subtract 8 dB and so the actual output in this case would be 40 dB. Alternatively, the 8 dB could be used in the calculation and interpretation of results and not in adjusting the signal level. If the user pushes the 3000 Hz fader to 30, then the signal is actually 38 dB. Minimum Audible Pressure at 3000 Hz is ISO defined as approximately −2 dB SPL, which means that the user's result is 40 dB below "Normal" at this frequency. Therefore, on the Audiogram, a point at 40 dB below 0 would be entered and displayed.

The data set in the form of deviations from the Sound Pressure Level that the headphones generated from that at 1 kHz are noted, and stored into the software program. For example, if the SPL generated by the headphones is 80 dB at 1 kHz but is 88 dB at 250 Hz, then a deviation of +8 dB is noted for this second frequency. This procedure is followed for all of the frequencies that are initially chosen to used by the system: 20, 60, 125, 250, 500, 750, 1 k, 1.5 k, 2 k, 3 k, 4 k, 5 k, 6 k, 8 k, 10 k, 12 k, 14 k, 16 k, 18 k, 20 kHz. Additional frequencies may be added, and/or these could be changed, provided the headphones are tested at the new frequencies.

Those familiar with the art will know that all Audiometric Couplers have their own frequency response characteristics, and those characteristics are generally known by the manufacturers of audiometric equipment. It is for this reason that the B&K 4153 coupler is used for measurement purposes here. This coupler is widely used, and is approved by both ANSI and IEC for the measurement of headphones. The same cannot be said for home made couplers.

The headphones are still connected to the RTA measurement system described above. For each headphone, a 1 kHz sine tone is sent to the left driver, and the signal level is adjusted via the volume control of the external amplifier to obtain a target calibration level of 94 dB SPL on the RTA. At this level, the voltage at the headphones is measured using a Hewlett-Packard 3501 RMS Voltmeter. This voltage is noted, and is used as the target voltage that is measured by the Calibrator. Different amplifiers of differing output impedances are used to drive the headphones, to verify the accuracy of measurements. No differences were obtained using different amplifier output impedances. Different target calibration levels, generated by respectively different voltages at the headphones, may be utilized.

In its current embodiment, the Beyerdynamic DT770 Pro headphones are used. They possess a nominal electrical impedance of 600 ohms, and they require an input voltage of 0.97 Volts at 1 khz to generate 94 dB SPL as measured by the measurement system used herein. Another headphone, the Sony MDR7506, with an impedance of 63 Ohms, requires a voltage of 0.1 Volts to generate 94 dB. In the current embodiment, a selector switch is provided on the Ear Q Calibrator to switch between these two selected headphones.

Figure 7A:
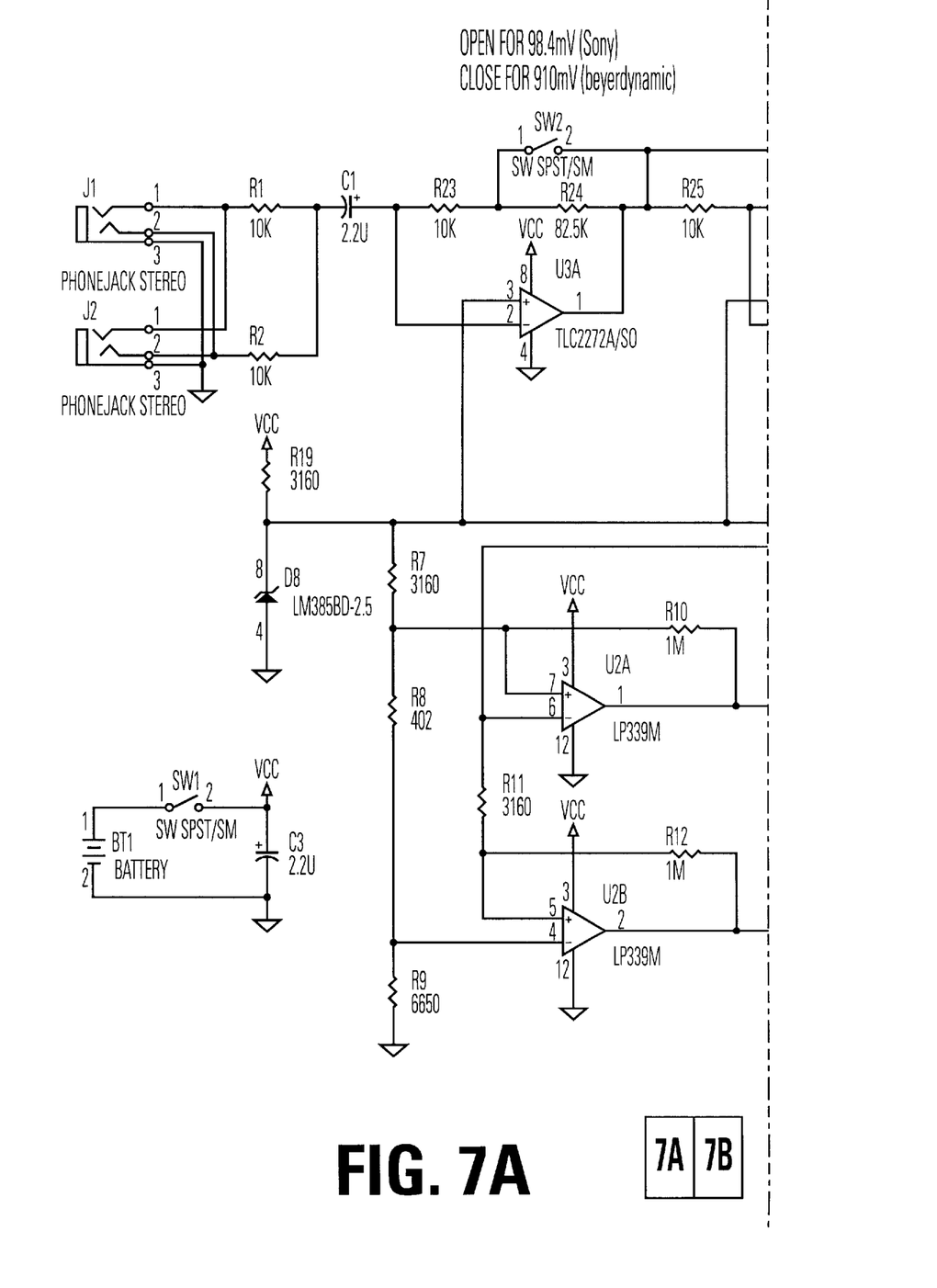
FIGS. 7A and 7B provide a circuit diagram of one example calibrator according to the present invention.
Figure 7B:
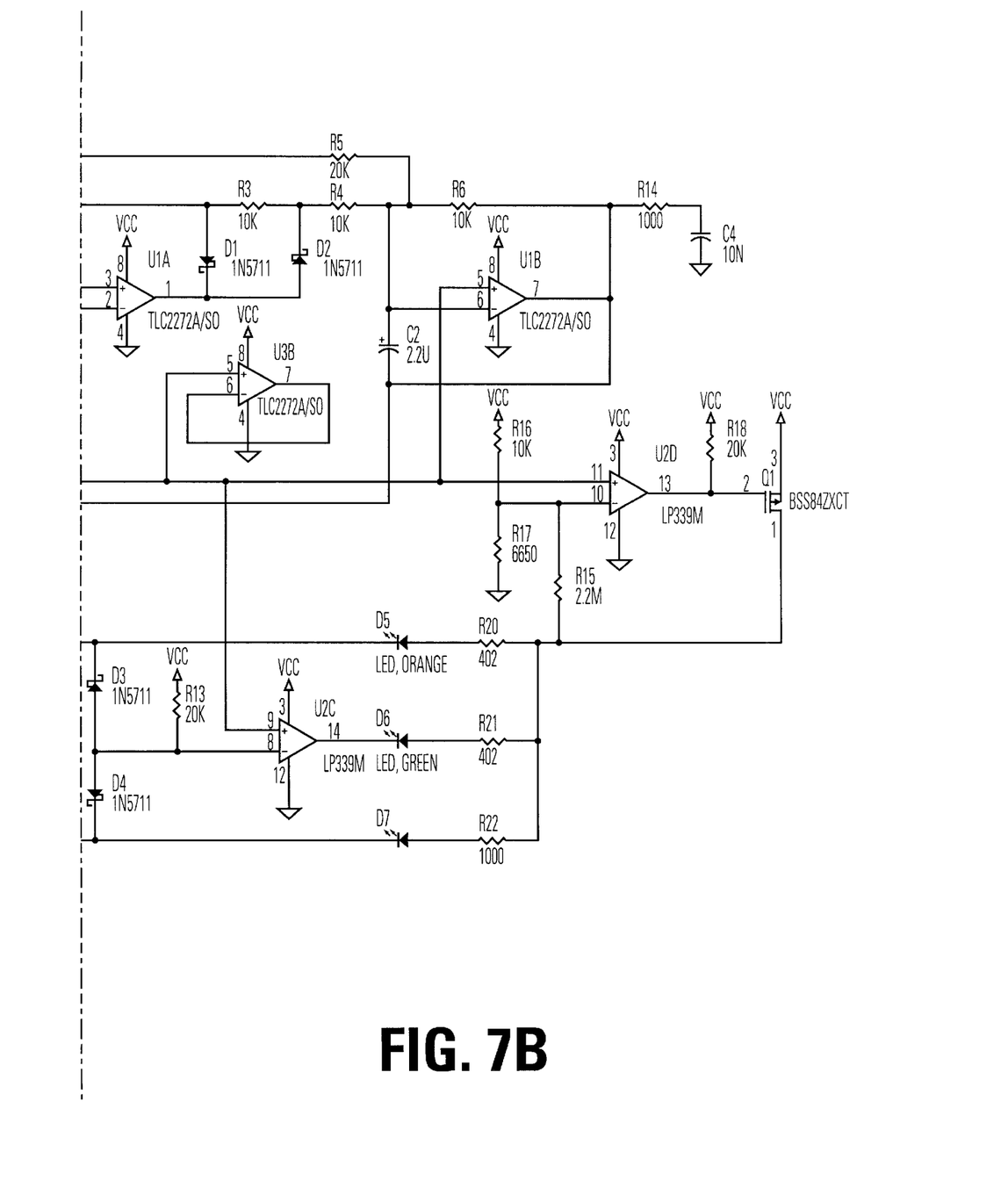

A circuit design is implemented as described below with reference to FIGS. 7A and 7B, that measures the voltage being delivered to the left driver of the headphones at 1 kHz. Three (3) indicator lights are employed to indicate Low (93 dB or lower); Correct (94 dB); or High (95 dB or higher) sound pressure Levels that are being generated by this input voltage. The circuit has a stereo input that is fed from an external amplifier (viz. headphone output from a recording studio mixing console). The actual manipulation of the input signal level to the calibrator, and hence the calibration of this invention, is controlled by the volume control of the external amplifier. (See FIG. 1) The circuit also has a stereo headphone output, into which the headphones are plugged. A breadboard prototype of the calibrator has been built, and tested for proper and accurate functioning. Bargraph or analogue meters may also be utilized to perform the indicator function. Other target calibration levels, and/or other headphones, may also be utilized, and it is also possible to include a range switch on the calibrator or in software to choose between different calibration values.

The circuit is designed to indicate the voltage that, for a specified headphone with a known impedance and known sensitivity, will generate 94 dB referenced to a B&K 4153 audiometric coupler. At its essence, the circuit provides for a heuristic evaluation of the signal level via a reference voltage provided by a 9 volt battery. There are comparator pathways to compare the input signal to this reference voltage, connected to indicator pathways that control indicator lights. The indicator lights are configured in a common-sense fashion; ie, a Yellow light indicates the voltage is too low by an amount that generates 1 dB short of the target SPL; a Green light indicates proper calibration voltage, such that the desired SPL is generated; and a Red indicator light indicates voltage that causes an excess of 1 dB over the target SPL to be generated. It has been shown using this heuristic circuit that calibration levels within 0.2 dB are repeatably and verifiably attained, if the amplifier's output is made as close as possible to that which causes the Red light to indicate while still causing the Green light to be on.

Software is implemented that allows the user to manually select and control the frequency and level of all signals generated by the computer's soundcard. The software provides 4 functions: Calibration; a Minimum Audibility Test (MAP test); a Dynamic Range Test; and Equal Loudness Perception Test. The software either automatically adjusts the actual output at each frequency to compensate for the frequency response of the headphones, or compensates for this frequency response during the compiling and display of the hearing test results. Additionally, the software allows the results of the tests to be stored both as screen snapshots and in chart/graph form. Each ear is tested individually for the MAP test, and both ears together for the other tests. Additional test procedures may be added.

All components (Computer; Amplifier; Calibrator; and Headphones) are connected together. As previously noted, the Amplifier may be a stand alone device such as a mixing console, or it may be a controllable part of the soundcard or computer. This is so, because the configuration of soundcards and computers varies enormously. The software first instructs the soundcard to generate a 1 kHz sine tone. The volume control of the amplifier is adjusted until the "Correct" indication is displayed by the calibrator. This level is now established (+1 dB) and defined as the full output level.

All modifications of audio signal levels are now accurate 1 dB attenuations downward from this full output level. These attenuations are accomplished by controlling the output level of the soundcard, or the level of the digital signal, or both. In its current embodiment, the MS Mixer Utility's and the digital signal level are both attenuated in tandem, to provide the greatest range of attenuation and yet maintain an audio signal that is essentially free from the harmonic distortion that otherwise occurs.

Figure 4:
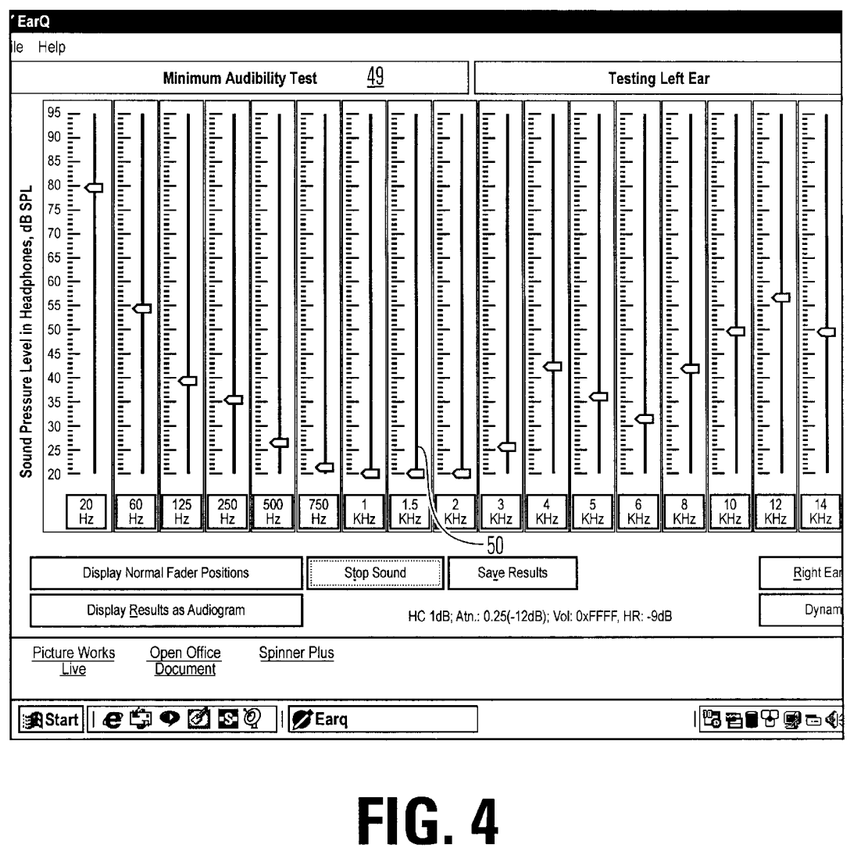
FIG. 4 is an illustration of a graphical user interface for use in a test according to the present invention.

Operation of Minimum Audible Pressure M.A.P. Test (also called minimum audibility test). The user is prompted by computer software controlling a graphical user interface such as shown in FIG. 4. The interface 49 includes a graphical construct having the appearance of a set of slider switches 50, or faders. At each selected frequency, the soundcard generates a sine tone that is warbled at +5% in frequency at a rate of 5 Hz. (Other warble characteristics may be employed, to reduce the effect of ear canal resonance on the measurement of high frequency perception). The output level of each individual frequency may be first offset by the appropriate deviation factor (as determined), or not. To determine the Minimum Audible Pressure at which any given frequency can be detected, the user adjusts the SPL output level of each frequency using the method of adjustment test procedure, by means of an onscreen "Mixing Console Fader" type of control via the mouse. The lowest position of each onscreen fader causes an output of 0 dB SPL, and the highest position of each fader causes an output of 94 dB SPL (these values may be adjusted to compensate for the response of the headphones). By using the method of adjustment, the user first pushes the onscreen fader upward to a position where the test tone signal can easily be heard. The fader is then pushed downward to where the test signal can not be heard. Finally, the fader is used to "zero in" on the lowest level at which the test signal can still be heard. It has been shown since Bekesy that the method of adjustment is a much faster procedure than a Forced Response procedure, and has greater test-retest reliability.

Figure 6:
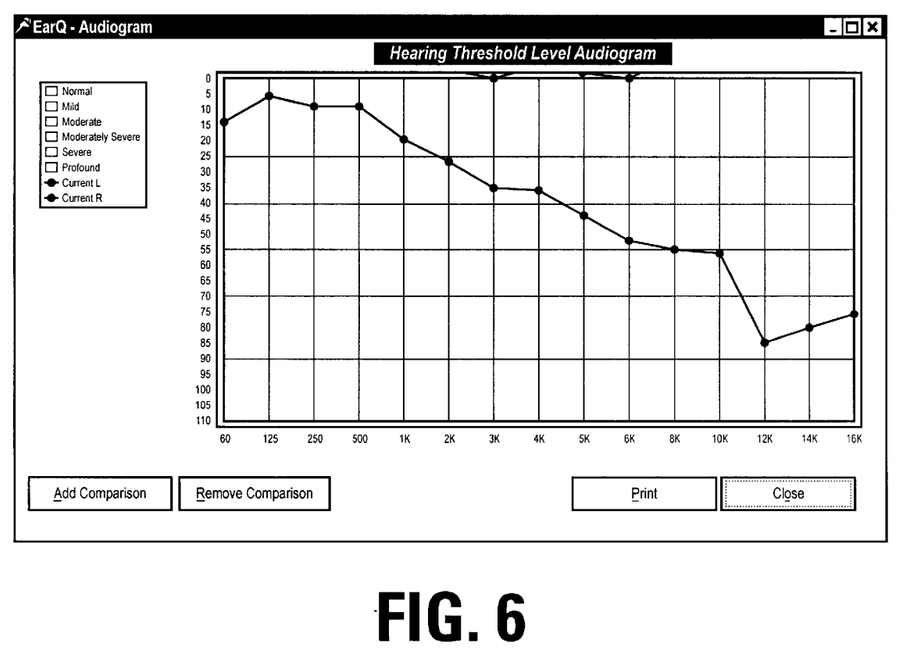
FIG. 6 is an illustration of a graphical audiogram presenting results of the testing according to the present invention.

For example: At 1 khz, if the onscreen fader reads "60 dB SPL," then that is the actual SPL in the headphones (as measured). However, in the same instance as cited above, at 250 Hz when the fader reads "60 dB," the actual SPL may still 60 dB because even though the headphones generate only 52 dB at that frequency, the software has corrected for the −8 dB deviation. Alternatively, the actual SPL is uncorted and is therefore 52 dB, but then when the software compiles and displays the hearing test results, this 8 dB compensation will be implemented. In its current embodiment, to maximize the dynamic range of computer soundcards, the latter option is implemented. This function occurs on all frequencies. The user adjusts the position of the onscreen faders for any or all frequencies for each ear. The results are stored and displayed both as fader positions and in chart or graph ("Audiogram") form, such as shown in FIG. 6. Normative data is implemented from clinical testing to establish all "normal" values and indicators.

To test an individual's dynamic range within the range of tested output levels, the user need only push the fader of each frequency all the way up and all the way down, noticing whether there is any point at which the perceived loudness gets very suddenly painful (which would indicate loudness recruitment or hyperacousis).

Figure 5:
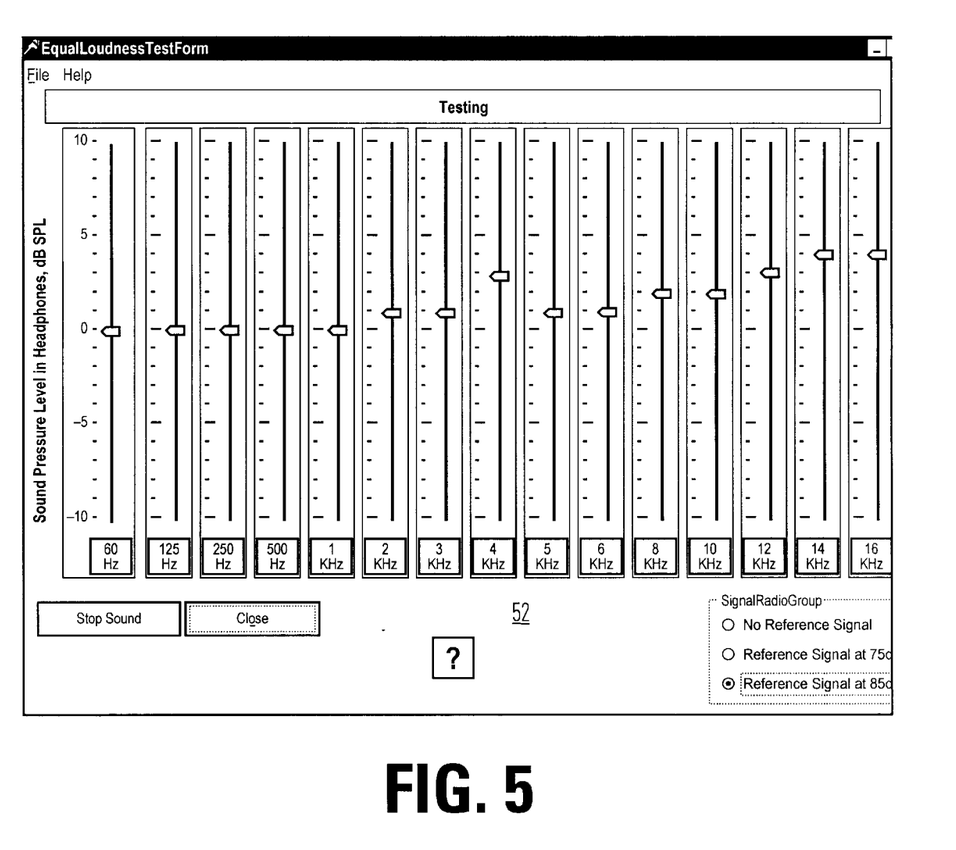
FIG. 5 is an illustration of an alternative graphical user interface for use in a test according to the present invention.

Equal Loudness tests: The software produces, or plays from a WAV file, 1/10 octave narrowband noise. The onscreen faders 52 for the equal loudness test such as shown in FIG. 5 are then adjusted to determined the user's loudness perception at each frequency as compared to a reference signal consisting of noise centered at 1 khz. This will inform the user whether he has relatively equal loudness perception (viz. the Equal Loudness Contour) over the entire range of frequencies. Normative data is obtained during clinical testing to establish all "normal" values and indicators for these procedures as well.

| LABEL | COMPONENT |
|---|---|
| BT1 | battery |
| C2 | 2.2 μF |
| C4 | 10 nF |
| D2 | IN5711 |
| D4 | IN5711 |
| D6 | LED-GREEN |
| D8 | LM385BD-2.5 |
| J2 | PHONEJACK STEREO |
| R1 | 10 KΩ |
| R3 | 10 KΩ |
| R5 | 20 KΩ |
| R7 | 3160Ω |
| R9 | 6650Ω |
| R11 | 3160Ω |
| R13 | 20 KΩ |
| R15 | 2.2 MΩ |
| R17 | 6650Ω |
| R19 | 3160Ω |
| R21 | 402Ω |
| R23 | 10 KΩ |
| R25 | 10 KΩ |
| SW2 | SW SPST/SM |
| U2 | LP339M |
| C1 | 2.2 μF |
| C3 | 2.2 μF |
| D1 | IN5711 |
| D3 | IN5711 |
| D5 | LED-ORANGE |
| D7 | LED-RED |
| J1 | PHONEJACK STEREO |
| Q1 | BSS84ZXCT |
| R2 | 10 KΩ |
| R4 | 10 KΩ |
| R6 | 20 KΩ |
| R8 | 402Ω |
| R10 | 1 MΩ |
| R12 | 1 MΩ |
| R14 | 1000 Ω |
| R16 | 10 KΩ |
| R18 | 20 KΩ |
| R20 | 402Ω |
| R22 | 1000Ω |
| R24 | 82.5 KΩ |
| SW1 | SW SPST/SM |
| U1 | TLC2272A/SO |
| U3 | TLC2272A/SO |

Overall, the present invention provides for a hearing test system that can be utilized in music studios or home environments having personal computers equipped with sound cards, and without special audiometric headphones. Furthermore the results are displayed a manner that is quick, easy and virtually foolproof as compared to prior art systems. For example, the minimum audibility test results are obtained from fader positions and then saved internally in software. The output is displayed in a simple graphic format. The display clearly shows the results of the test relative to normal hearing.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the appended claims.

What is claimed is:

1. A method for performing a hearing test using a system including a computer producing audio signals, headphones, and volume control for the audio signals, wherein the headphones are characterized by a data set including drive voltages for corresponding test frequencies at which a constant sound pressure level is generated by the headphones, and a calibrated drive voltage at a particular reference frequency which produces a particular sound pressure level output by the headphones, the method comprising:

coupling audio signals from the computer to an input of a calibration device which translates an input drive voltage to an output drive voltage;

coupling the headphones to the output drive voltage of the calibration device;

setting the output of the system to the particular reference frequency;

adjusting the volume control for the audio signals at the particular reference frequency until the calibration device produces the calibrated drive voltage;

with the volume control set for the system at the adjusted level, prompting a user through a hearing test in the test frequencies, and compensating according to the data set characterizing the headphones.

2. The method of claim 1, wherein said prompting includes displaying a graphical user interface to the user supporting a method of adjustment test procedure.

3. The method of claim 1, wherein said particular reference frequency is about 1 kHz.

4. The method of claim 1, wherein said hearing test comprises a minimum audibility test.

5. The method of claim 1, wherein said hearing test comprises an equal loudness test.

6. The method of claim 1, including providing an indicator light on the calibration device which indicates when the calibration device is producing the calibrated drive voltage, and wherein said adjusting includes adjusting the volume control until the indicator light is illuminated.

7. The method of claim 1, including providing a first indicator light on the calibration device indicating that the output drive voltage of he calibration device is below the calibrated drive voltage, a second indicator light on the calibration device indicating that the output drive voltage of the calibration device is about equal to the calibrated drive voltage, and a third indicator light on the calibration device indicating that the output drive voltage of the calibration device is above the calibrated drive voltage; and wherein said adjusting includes adjusting the volume control until the second indicator light is illuminated.

8. The method of claim 1, wherein said prompting includes displaying a graphical input construct appearing like a set of sliders for a set of frequencies; and outputting tones corresponding to frequencies in the set of frequencies in response to adjustment by the user of an indicator on the graphical input construct for the tones.

9. The method of claim 1 including displaying results of the hearing test.

10. The method of claim 1, including displaying an audiogram indicating results of the hearing test.

11. An apparatus for conducting a hearing test using a system including computer producing audio signals for audio transducers, headphones, and volume control for the audio signals, wherein the headphones are characterized by a data set including drive voltages for corresponding test frequencies at which a constant sound pressure level is generated by the headphones, and a calibrated drive voltage at a particular reference frequency which produces a particular sound pressure level output by the headphones, the apparatus comprising:

a calibration device, having an input coupled to receive the audio signals produced by the computer, and to supply output drive voltages to the headphones, the calibration device including an indicator which indicates when the output drive voltage equals about the calibrated drive voltage; and a computer program stored in machine readable medium, including the data set characterizing the headphones, and software executable by the computer system, arranged to prompt a user through a hearing test in the test frequencies, and compensating according to the data set characterizing the headphones.

12. The apparatus of claim 11, wherein said software includes routines for displaying a graphical user interface to the user supporting a method of adjustment test procedure.

13. The apparatus of claim 11, wherein said particular reference frequency is about 1 kHz.

14. The apparatus of claim 11, wherein said hearing test comprises a minimum audibility test.

15. The apparatus of claim 11, wherein said hearing test comprises an equal loudness test.

16. The apparatus of claim 11, wherein the indicator includes a plurality of indicator lights on the calibration device which indicate when the calibration device is producing drive voltages near the calibrated drive voltage.

17. The apparatus of claim 11, wherein said indicator includes a first indicator light on the calibration device indicating that the output drive voltage of the calibration device is below the calibrated drive voltage, a second indicator light on the calibration device indicating that the output drive voltage of the calibration device is about equal to the calibrated drive voltage, and a third indicator light on the calibration device indicating that the output drive voltage of the calibration device is above the calibrated drive voltage.

18. The apparatus of claim 11, wherein said software includes routines for displaying a graphical input construct appearing like a set of sliders for a set of frequencies; and outputting tones corresponding to frequencies in the set of frequencies in response to adjustment by the user of an indicator on the graphical input construct for the tones.

19. The apparatus of claim 11, wherein said software includes routines for displaying results of the hearing test.

20. The apparatus of claim 11, wherein said software includes routines for displaying an audiogram indicating results of the hearing test.

* * * * *